Aug. 8, 1944. F. H. HOWARD Plant Pat. 636
ROSE PLANT
Filed Dec. 17. 1943
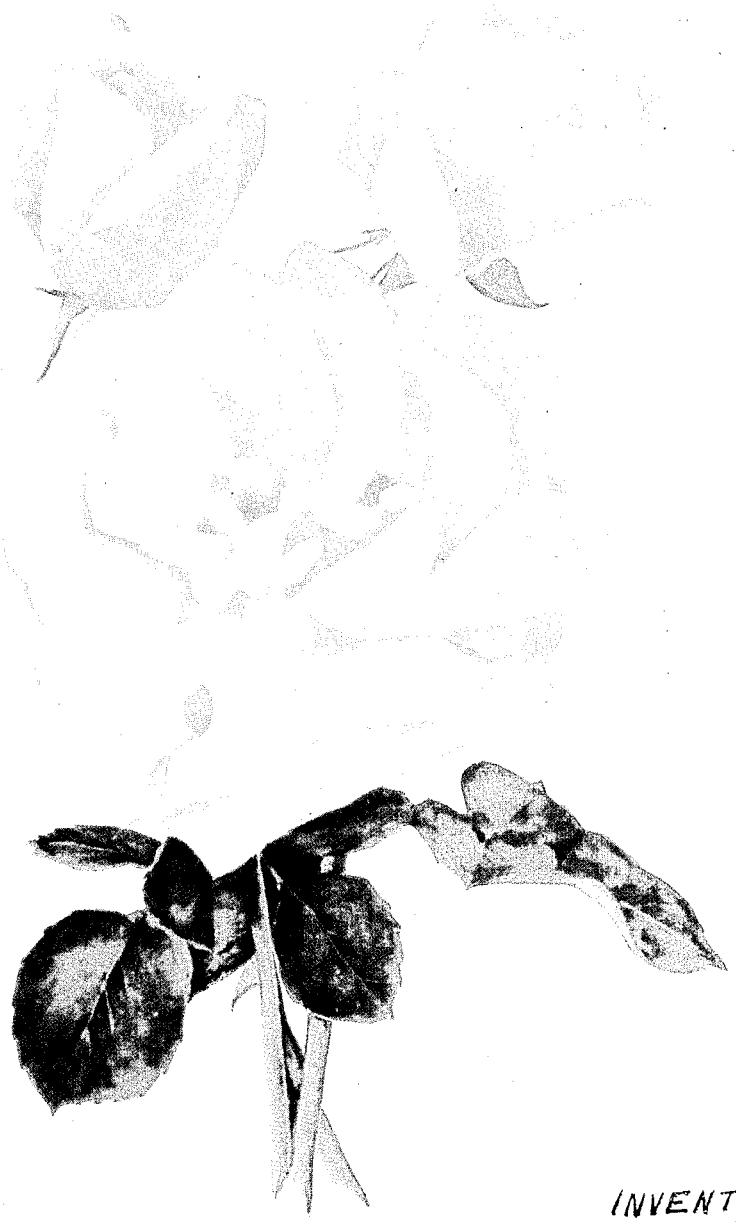
INVENTOR
Frederick Huber Howard
By Orville M Kile
Plant Pat. Agt.

Patented Aug. 8, 1944

Plant Pat. 636

UNITED STATES PATENT OFFICE

636

ROSE PLANT

Frederick Huber Howard, Montebello, Calif.

Application December 17, 1943, Serial No. 514,701

1 Claim. (Cl. 47—61)

My present invention relates to a new and distinct variety of hybrid tea rose plant which resulted from a cross between Miss Rowena Thom and an unnamed seedling at my greenhouses at Montebello, California.

The plant is one of tremendous vigor, in this climate reaching a height of 5 to 6 feet in a single season. It is a fact the most vigorous of any variety in a field of over 150,000 various hybrid tea plants. It is also exceedingly healthy and disease resistant. It is almost entirely free from thorns for at least three-fourths the length of its canes, and has very few thorns even on the remainder of the length.

This variety has a large two-toned bloom of outstanding beauty and keeping qualities. Its flower coloring is similar to that of Pink Radiance although more definitely contrasting and the dark tone is more intense. The bud is long and pointed. Although of entirely different parentage from the Pink Radiance, it might be considered an improved Pink Radiance with stronger growth, better coloring, and much better shaped bud and flower.

The illustrations making a part of this specification show in approximately their true colors, three specimens of my new variety in various stages of opening, together with portions of the stems and foliage.

The following detailed description is made from field grown specimens. Color references are to Ridgway's Color Standards and Nomenclature. Observations were made from flowers shipped from Montebello, California, at 6:00 p. m. October 18th and received at Washington, D. C., at 4:00 p. m. on October 20th. Most of the observations were made about an hour after receipt of flowers. Some of these same flowers lasted for an entire week after their receipt in Washington.

*The plant*

Growth: Exceedingly vigorous. Attains a height of 5 to 6 feet in a single season.

Blooming habit: Continuous and prolific bloomer.

Form: Tall, upright bush.

Foliage: Compound, with 3 to 7 leaflets.

*Size.*—Small to medium. Terminal leaflet 2 inches long, ½ inch wide. Lateral leaflets much smaller.

*Color.*—Very dark, approximately Dark Cress Green (Pl. XXXI) or even darker on upper surface. The under surface is approximately Light Cress Green (Plate XXXI).

*Aspect.*—Glossy on upper surface; dull on under surface. Central vein very prominent, other veins hardly discernible.

*Shape.*—Long oval with pointed apex.

*Edge.*—Very finely serrated.

*Texture.*—Leathery and smooth.

*Rachis.*—Very short; red and grooved above; under side smooth and green.

*Stipules.*—Broad; short; clinging.

*Stems.*—Strong; upright, but slightly staggered. Internodes short. Color approximately Oil Green (Plate V). Thorns almost entirely missing, there being only a few at the basal portion of the stems.

Disease resistance: Remarkably free from mildew and blackspot.

*The flower*

Bud:

*Size.*—Up to 3 inches in length.

*Shape.*—Just before and just after calyx breaks, bud is a long, slender cone shape. The opening bud is long and slender, changing to urn shape just before opening. Does not bullhead in dull weather.

*Color.*—When calyx breaks, approximately Eugenia Red (Plate XIII). Half open bud is Spinel Pink (Plate XXVI) or slightly darker.

*Sepals.*—Slightly foliaceous. Reflex early.

Flower:

*Size.*—Large. Fully opened, it is approximately 5 inches in diameter.

*Form.*—At first it is urn shaped, then somewhat globular, retaining its rounded form. Some of the outer petals usually roll back slightly but the central petals remain folded over the stamens which are not visible unless the petals are pushed aside. Although there are relatively few petals, it has the effect of a heavy rose because of this feature of retaining its deep, rounded form, and at the same time having the center covered with a folded petal or two.

*Petalage.*—The petalage varies rather widely in different specimens, but the average is about 24.

*Color.*—The flower is distinctly two-toned, the inner surface of the petals being a pale pink approximately Rose Pink (Plate XII), and the outer surface being approximately Spinel Pink (Plate XXVI) later changing to a color between Deep Rose Pink and Tyrian Pink (Plate XII).

*Fragrance.*—Highly fragrant with a lasting fragrance.

*Longevity.*—Flower last an exceedingly long time and in perfect condition. As a cut flower it often lasts more than a week in ordinary room temperatures.

Reproductive organs:

*Pistils.*—Many; tightly bunched; set high. *Styles*—dark red on exposed portion. *Stigmas*—greenish yellow.

*Stamens.*—Many; surround pistils. *Filaments*—unequal lengths and irregularly curved, making a ragged appearance. *Anthers*—medium in size and dark yellow.

Having thus disclosed my invention, I claim:

The new and distinct variety of hybrid tea rose plant substantially as herein shown and described, characterized particularly by its exceedingly vigorous and healthy growth, its virtual thornlessness; its long, slender buds; and its perfectly formed, fragrant, exceedingly long-lasting flowers of dual tones as indicated.

FREDERICK HUBER HOWARD.

CERTIFICATE OF CORRECTION.

Plant Patent No. 636. August 8, 1944.

FREDERICK HUBER HOWARD.

It is hereby certified that error appears in the above numbered patent requiring correction as follows: In the printed specification, first column, line 1, beginning with "My present invention" strike out all to and including the word and period "indicated.", page 2, second column, line 8, and insert instead the specification shown below -

My present invention relates to a new and distinct variety of hybrid tea rose plants which originated from a cross between Mrs. J. D. Eisele and Condessa de Sastago. The resulting variety has been asexually reproduced and its distinguishing qualities have proved to be firmly fixed.

My new variety is exceedingly free in bloom and is practically disease-proof. The flower is camellia-like in form and is an exceedingly attractive shade of rose somewhat suffused with orange.

The illustrations making a part of this specification show three specimens of the flower of this new variety in varying stages of opening and in approximately their true colors. It must be understood, however, that this coloring is very difficult to portray with the mediums at hand.

Following is a detailed description of the plant and flower of this new variety. Color references indicate Ridgway's Color Standards and Nomenclature.

*The plant*

Growth: Vigorous and very healthy.

Form: Bushy grower, but tall. When fully developed, a total plant is composed of many separate upright bushy branches.

Blooming habits: It is a true remontant type of rose, furnishing blooms from early spring to advent of frosts. It is exceedingly free blooming, a fully developed plant producing at least 50 blooms per year.

Stems: Sturdy; upright; usually tinged with red tones, approximately Brick Red (Plate XIII); has many thorns.

*Thorns.*—Sharp; large but relatively short; slightly downward-pointing; red-tinged; irregularly spaced, sometimes bunched.

Foliage: Compound, usually with 3 to 5 leaflets.

*Size.*—Medium. Terminal leaflet approximately 2 inches long by 1½ inches wide.

*Texture.*—Leathery.

*Shape.*—Oval, with broad base and pointed apex.

*Color.*—Approximately Forest Green (Plate XVII).

Rachis: Slender and grooved above; occasional spines below.

Stipules: Clinging and very small.

Disease resistance: Practically disease-proof, particularly resistant to blackspot.

*The flower*

Bud:

*Color of small bud.*—Pomegranate Purple (Plate XII) to Carmen (Plate I).

*Color of expanding bud.*—The color is not shown in Ridgway's Color Standards and Nomenclature but would fall between Begonia Rose and Scarlet (Plate I).

*Shape.*—Oval, with broad base and pointed apex. Opening somewhat globular.

*Size.*—Five-eighths inch broad at base, about the same or slightly less in length, just before calyx breaks. When calyx breaks bud is about ¾ inch in each dimension. The half open bud is 1½ inches to 2 inches in length.

Flower:

*Size.*—Medium, 3 to 3½ inches across when fully open.

*Form.*—Beautifully and perfectly formed in loose cup-shape. This form is retained for a considerable time but later opens somewhat camellia-like. Petals reflex early.

*Petalage.*—Double, numbering about 45.

*Texture.*—Medium.

*Fragrance.*—Delightful and very pronounced.

*Color.*—The outer petals retain the coloring of the bud until the flower is fully open. The nearest in Ridgway's is Rose Doree (Plate I), but usually a little darker than that shade and suffused with Scarlet (Plate I) in the central portion of the petal. There is a large aiglet of Light Cadmium (Plate IV). The inner surface of the petals is lighter. When the rose is older and fully opened, the color changes to uniformly Deep Rose Pink (Plate XII) except that the yellow aiglet is retained.

*Shape of petals.*—Outer petals slightly longer than wide. Edge smooth. Inner petals narrower and smaller.

*Persistence of petals.*—Cling until dead.

*Lasting quality.*—Very good, flowers often lasting a full week in the cut state.

Reproductive organs:

*Pistils.*—Many; tightly bunched; set high; irregular lengths with longest in center. *Styles*—white; tipped with Red. *Stigmas*—light yellow.

*Stamens.*—Moderate number; arranged around bunched pistils. *Filaments*—red; uneven in length. *Anthers*—rather large; deep yellow (approximately Primuline Yellow (Plate XVI).

Having thus disclosed my invention, I claim:

The new and useful variety of hybrid tea rose plant, substantially as shown and described, characterized by its great resistance to disease; its vigorous upright and bushy growth; its strong leathery foliage; its exceedingly prolific production of beautifully formed flowers of very pronounced fragrance, excellent lasting qualities and pleasing, distinctive color as indicated.

and that the said Letters Patent should be read with this correction therein that the same may conform to the record of the case in the Patent Office.

Signed and sealed this 12th day of September, A. D. 1944.

Leslie Frazer (Seal) Acting Commissioner of Patents.